(12) United States Patent
Hutchinson et al.

(10) Patent No.: US 10,984,145 B1
(45) Date of Patent: Apr. 20, 2021

(54) USING MACHINE LEARNING TO EXPLORE FORMULATIONS RECIPES WITH NEW INGREDIENTS

(71) Applicant: Citrine Informatics, Inc., Redwood City, CA (US)

(72) Inventors: Maxwell Lipford Hutchinson, Pittsburgh, PA (US); Edward Soo Kim, Medicine Hat (CA); Ryan Michael Latture, San Francisco, CA (US); Sean Phillip Paradiso, Redwood City, CA (US); Julia Black Ling, Redwood City, CA (US)

(73) Assignee: CITRINE INFORMATICS, INC., Redwood City, CA (US)

( * ) Notice: Subject to any disclaimer, the term of this patent is extended or adjusted under 35 U.S.C. 154(b) by 0 days.

(21) Appl. No.: 16/935,077

(22) Filed: Jul. 21, 2020

(51) Int. Cl.
*G06K 9/62* (2006.01)
*G06F 30/12* (2020.01)
(Continued)

(52) U.S. Cl.
CPC ........ *G06F 30/12* (2020.01); *G06F 16/24578* (2019.01); *G06F 16/9024* (2019.01);
(Continued)

(58) Field of Classification Search
CPC ............. G06T 7/0012; G06T 7/0083; G06T 2207/30004; G06T 7/0081; G06T 2207/10116; G06T 5/40; G06T 2207/30068; G06T 7/0085; G06T 7/60; G06T 7/12; G06T 7/11; G06T 7/174; G06T 1/00; G06T 7/00; G06T 7/0016; G06T 7/13; G06F 19/321; G06F 30/12;
(Continued)

(56) References Cited

U.S. PATENT DOCUMENTS

| 10,366,779 B2 * | 7/2019 | Hsu ........................ G16C 20/70 |
| 2003/0078740 A1 * | 4/2003 | Kieken ................ B01J 19/0046 702/30 |
| 2020/0210635 A1 | 7/2020 | Washburn et al. |

OTHER PUBLICATIONS

Jha, D. et al., "ElemNet: Deep Learning the Chemistry of Materials from Only Elemental Composition," Scientific Reports, vol. 8, Dec. 4, 2018, pp. 1-13.
(Continued)

*Primary Examiner* — Duy M Dang
(74) *Attorney, Agent, or Firm* — Fenwick & West LLP

(57) ABSTRACT

A system and a method are disclosed that, in an embodiment, receive first input from a user of a candidate formulation recipe, and second input from the user of target properties and target property constraints. The system inputs the first input into a machine learning model, the model having been trained using historical training data, each element of the historical training data corresponding to a known formulation having a known feature representation, each known formulation having associated properties and statistical representations of each feature of the known formulation that form the known feature representation. The system receives as output from the model a predicted property of a candidate formulation derived using the first input and the likelihood that the candidate formulation satisfies the target property constraints using the second input. The system generates for display to the user a predicted likelihood that the predicted property satisfies the second input.

20 Claims, 7 Drawing Sheets

(51) Int. Cl.
  *G06F 16/901* (2019.01)
  *G06F 16/2457* (2019.01)
  *G06N 20/00* (2019.01)
(52) U.S. Cl.
  CPC ......... *G06K 9/6232* (2013.01); *G06K 9/6256* (2013.01); *G06N 20/00* (2019.01)
(58) Field of Classification Search
  CPC ............. G06F 16/9024; A61B 5/02007; A61B 5/7264; A61B 5/742; G06K 9/4604; G06K 9/52; G06K 9/6267; G06K 9/66; G06K 9/6232; G06K 9/6256; G01N 33/4833; G01N 33/48; G01N 33/5091; G06N 20/00; G06N 20/10; G06N 20/20
  See application file for complete search history.

(56) References Cited

OTHER PUBLICATIONS

Swischuk, R. et al., "Projection-based model reduction: Formulations for physics-based machine learning," Computers and Fluids, Aug. 2018, pp. 1-14.
Yang, Y. et al., "Deep learning for in vitro prediction of pharmaceutical formulations," Acta Pharmaceutica Sinica B, vol. 9, Iss. 1, Jan. 2019, pp. 177-185.

\* cited by examiner

USING MACHINE LEARNING TO EXPLORE FORMULATIONS RECIPES WITH NEW INGREDIENTS

TECHNICAL FIELD

The disclosure generally relates to the field of machine learning, and more particularly relates to exploring chemical formulations engineering using machine learning.

BACKGROUND

Formulations producers may need to create new formulations to achieve performance specifications for various properties (e.g., mechanical, optical, electrical, chemical, etc.) that are required for a given application. These properties may vary based on the recipe used to create the formulation. In some instances, formulations producers may consider using untested ingredients in a formulation. For example, if ingredients for an existing formulation become unavailable or costly (e.g., due to a supply chain failure), the producer may wish to design a recipe using new ingredients. However, experimentation with new ingredients may be prohibitively expensive, may be inefficient, and may have no guarantee of success in achieving necessary performance specifications.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

One embodiment of a disclosed system, method and computer readable storage medium includes using machine learning to model performance of formulations where recipes include previously untested ingredients. In an embodiment, the system may receive first input from a user, the input including of candidate formulation recipes and/or processing parameters, and second input from the user of one or more target properties and associated constraints. The system may input the first input into a machine learning model, the machine learning model having been trained using historical training data, each element of the historical training data corresponding to a known formulation having a known feature representation, each known formulation having associated properties and statistical representations of each feature of the known formulation that form the known feature representation. The system may then receive as output from the machine learning model the predicted properties of a candidate formulation. The system may determine and output the candidate formulation's predicted properties and the likelihood of satisfying the target property constraints for display to the user.

System Environment for New Recipe Evaluation Service

Figure 1:
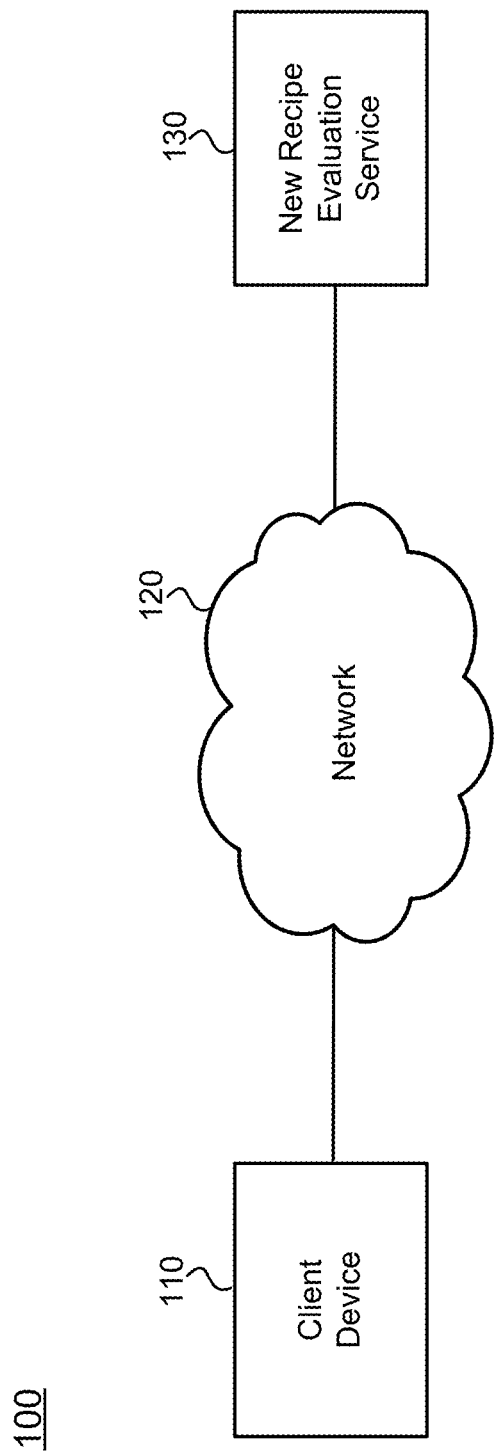
FIG. 1 illustrates one embodiment of a system environment for operating a new recipe evaluation service.

FIG. 1 illustrates one embodiment of a system environment for operating a new recipe evaluation service. Environment 100 includes client device 110, network 120, and new recipe evaluation service 130. Client device 100 may be any device of a user, such as a smartphone, laptop computer, tablet, personal computer, or any other device operable by a user. Client device 100 may transmit a request over network 120 (e.g., the Internet, or any other data communications network) to new recipe evaluation service 130. The request may include candidate formulation recipes and their processing parameters. The request may also include one or more desired performance specifications of a formulation that uses the ingredients. New recipe evaluation service 130 may take the request and may return to the user a plurality of predicted performances of one or more candidate formulations. Further details of how new recipe evaluation service 130 operates are disclosed below with respect to FIGS. 2-7.

Particulars of the New Recipe Evaluation Service

Figure 2:
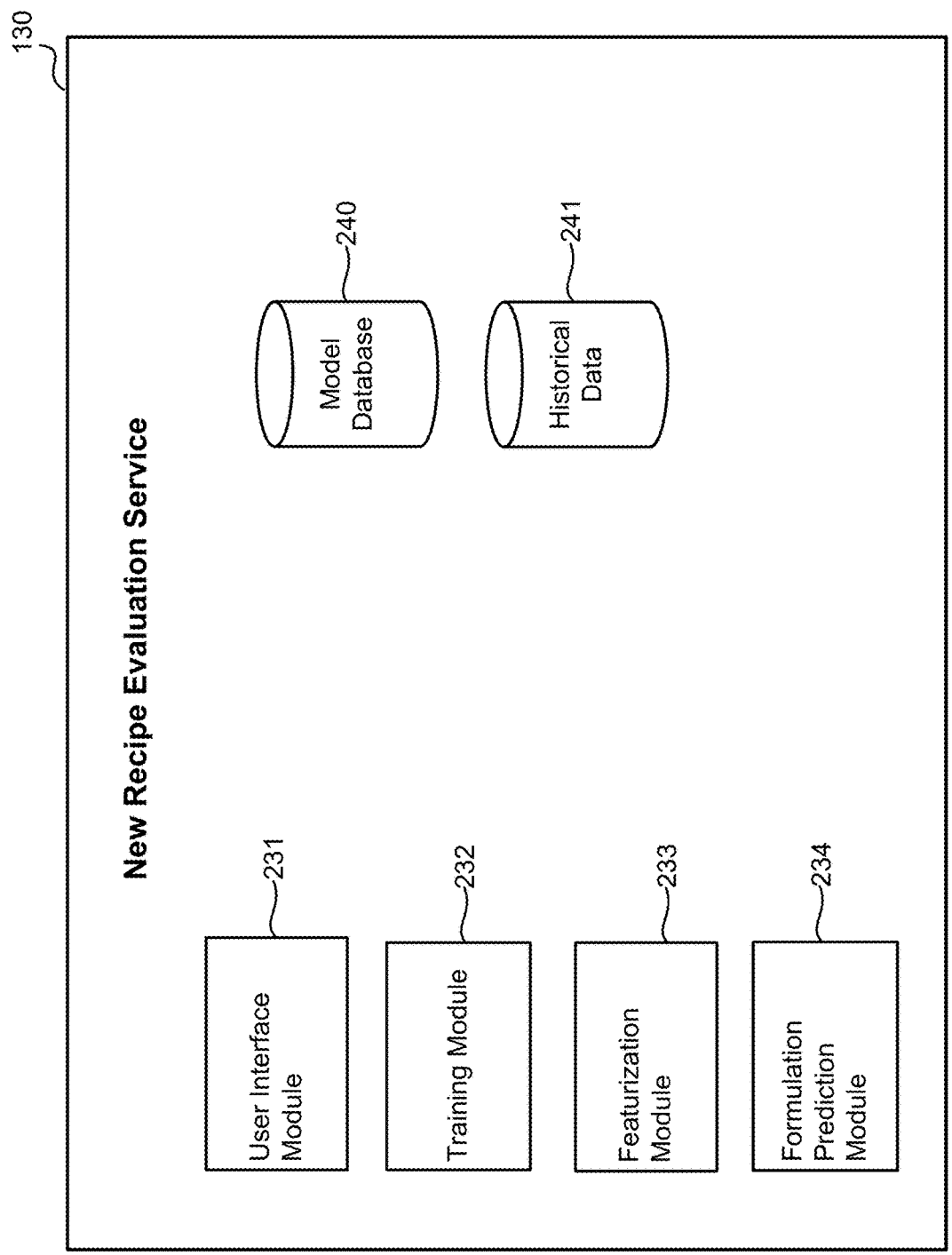
FIG. 2 illustrates one embodiment of exemplary modules and databases used by the new recipe evaluation service.

FIG. 2 illustrates one embodiment of exemplary modules and databases used by the new recipe evaluation service. New recipe evaluation service 130 includes user interface module 231, training module 232, featurization module 233, formulation prediction module 234, model database 240, and historical data 241. The modules and databases depicted with respect to new recipe evaluation service 130 are merely exemplary; more or fewer modules and/or databases may be used to achieve the functionality described herein. Moreover, some or all of new recipe evaluation service may be distributed across multiple servers and/or may be on-board client device 110. For example, an application may be installed on client device 110, or accessed by way of a browser of client device 110, that includes some or all of the functionality of new recipe evaluation service 130. As one example, user interface module 231 may be instantiated on client device 110 (e.g., using an installed application), whereas training module 232, featurization module 233, and formulation prediction module 234 may be installed using one or more servers remote from client device 110.

The term recipe, as used herein, may refer to a prescription of how to generate a formulation. This prescription may include ingredients used, statistical representations of amounts of each ingredient used, processing parameters (e.g., directions on how to manipulate the ingredients, such as how long to heat some combination of the ingredients and at what temperature), mixing information (e.g., which ingredients to mix together and in what fashion and in what order), and so on. The term ingredient as used herein may refer to raw materials used that, together, when the recipe is followed, yield a formulation. The terms "new ingredient" and "untested ingredient" refer to ingredients for which the user has insufficient performance data (e.g., not enough or no existing formulation performance data). For example, the user may have ingredient property data (e.g. ingredient density or ingredient composition), but may not have formulation property data for recipes including this ingredient. The term target property, as used herein, may refer to a performance property of a formulation (e.g., tensile strength, optical clarity, electrical conductivity, and so on). The term constraint, as used herein, may refer to a performance requirement of a formulation (e.g., the formulation must have a tensile strength of at least 95 megapascals).

User interface module 231 causes a display to be provided to the user for inputting data, such as training data, formulation recipes and processing parameters, target properties and constraints, and the like. With respect to training a machine learning model, user interface module 231 may prompt the user to input training data, including a formulation, the component ingredients of the formulation, the processing parameters associated with the formulation recipe, and the performance properties achieved by the formulation. With respect to predicting new formulations, user interface module 231 may prompt the user to input one or more target properties and associated constraints on those target properties. User interface module 231 may be used to output results, such as the predicted properties of candidate formulations. Any inputs or outputs to a user interface described herein may be managed by user interface module 231.

Training module 232 trains a machine learning model for predicting the properties of formulations. In an embodiment, one or more generic models may be used that are trained to predict the properties of formulations, and in such embodiments training module 232 need not be used. In some embodiments, generic models may be unavailable, or may be available and may be augmented using training data of a user in order to improve their precision. Training module 232 may be used to train a machine learning model where generic models are unavailable, or where they are available but may be supplemented with user training data.

Figure 3:
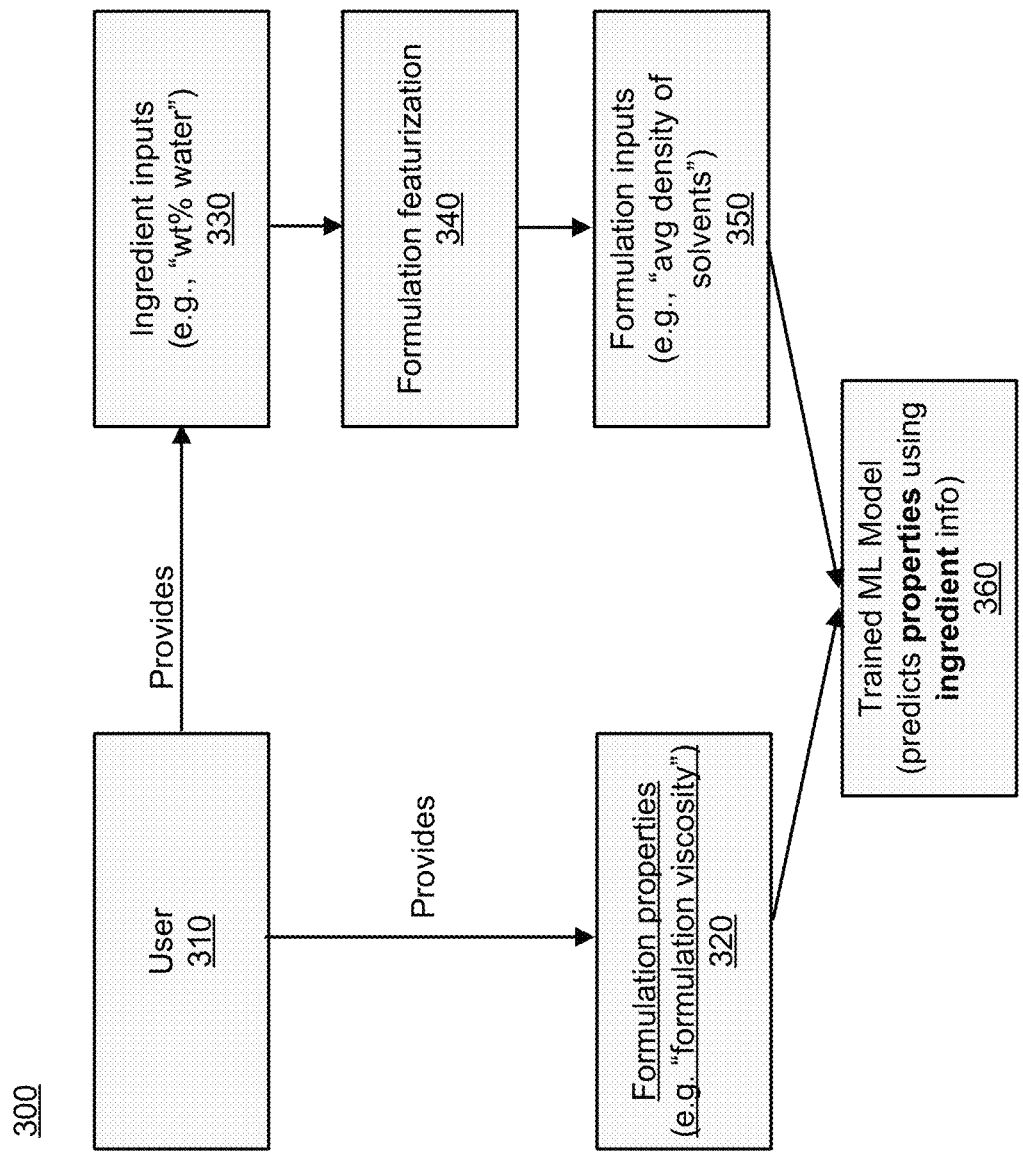
FIG. 3 is a data flow diagram illustrating an exemplary embodiment of training a machine learning model used by the new recipe evaluation service.

Turning briefly to FIG. 3 for illustration of an exemplary training process, FIG. 3 is a data flow diagram illustrating an exemplary embodiment of training a machine learning model used by the new recipe evaluation service (e.g., to freshly train a machine learning model, or augment a generic machine learning model). Data flow 300 begins with a user 310 providing two inputs, input 320 and input 330. Input 320 includes formulation properties, such as performance specifications. For example, the user may have previously experimented with creating rubber formulations using natural rubbers, colorants, and curing agents. The formulation properties of these rubber formulations include performance specifications such as mechanical properties, like impact strength and tear strength. These performance specifications may be input as input 320.

Input 330 includes the recipe of ingredients that, taken together (and processed as specified), create the formulation. For example, this might include each raw material and/or chemical, as well as a statistical representation of their amounts used, in the formulation. This might also include known physical properties of those ingredients. It could also include processing information. For example, this might include the types and amounts of natural rubbers, colorants, and curing agents used in creating the rubber, the curing temperature and time of the rubber, as well as the density, color, or chemical composition of those rubbers, colorants and curing agents. Amounts may be raw amounts (e.g., in terms of weight or volume of each ingredient), percentages or ratios (e.g., 90% natural rubber, 3% colorant, 6% curing agent 1, 1% curing agent 2), or any other form of statistical representation. Input 330 may also include the role of each ingredient (that is, where an agent that turns rubber blue is used, that agent is indicated as having a role of "colorant").

Input 330 is used to generate formulation featurization 340. The term formulation featurization, as used herein, may refer to transforming each ingredient into its features, the features together representing a makeup or properties of their corresponding ingredient. For example, rather than representing a formulation in terms of an amount of rubber, colorant, and curing agent, the formulation can be represented by the average particle size of colorants in the formulation, a total amount of different curing agents in the formulation, and so on. Stated another way, imagine an example where a cake is baked using a cup of flour, half a cup of sugar, and a stick of butter. Rather than representing the cake in terms of an amount of flour and sugar, the attributes of flour and sugar can be transformed into, for example, an amount of fat in the cake, the average viscosity of the liquids in the cake batter, among other material and chemical properties of the cake, that are caused to exist based on the raw ingredients of the cake.

In order to generate formulation featurization 340, featurization module 233 may apply homogenous mixture featurization. Featurization module 233, for example, may featurize a formulation by taking the weighted average of the properties of the ingredients m, raised to a power p, and grouped by component type C. The weighted average may be weighted by composition fraction, w. An exemplary homogenous mixture featurization equation follows:

$$m_C = \left( \frac{1}{w_C} \sum_{i \in C} w_i m_i^p \right)^{1/p}$$

Formulation featurization 340 results in features of the formulation, which include formulation inputs 350. Formulation inputs 350 pair with inputs 320 as training data for trained machine learning model 360. Trained machine learning model 360 may then receive inputs including ingredient information, and may output predictions of properties based on features of the input ingredient information. Trained machine learning model 360 may be stored to model database 240. Moreover, rather than manually inputting historical data, the user may instead provide formulation data in bulk to new recipe evaluation service 130, which may store the data in historical data database 241. Historical data used to train the machine learning model may be proprietary in nature and the user may not want to share the historical data or the resulting machine learning model for use by others. To this end, user interface module 231 may be used by the user to configure privacy settings, such as opting in or out of sharing (a default may be opting out). Where historical data is shared, a generic machine learning model may be augmented using the historical data.

Figure 4:
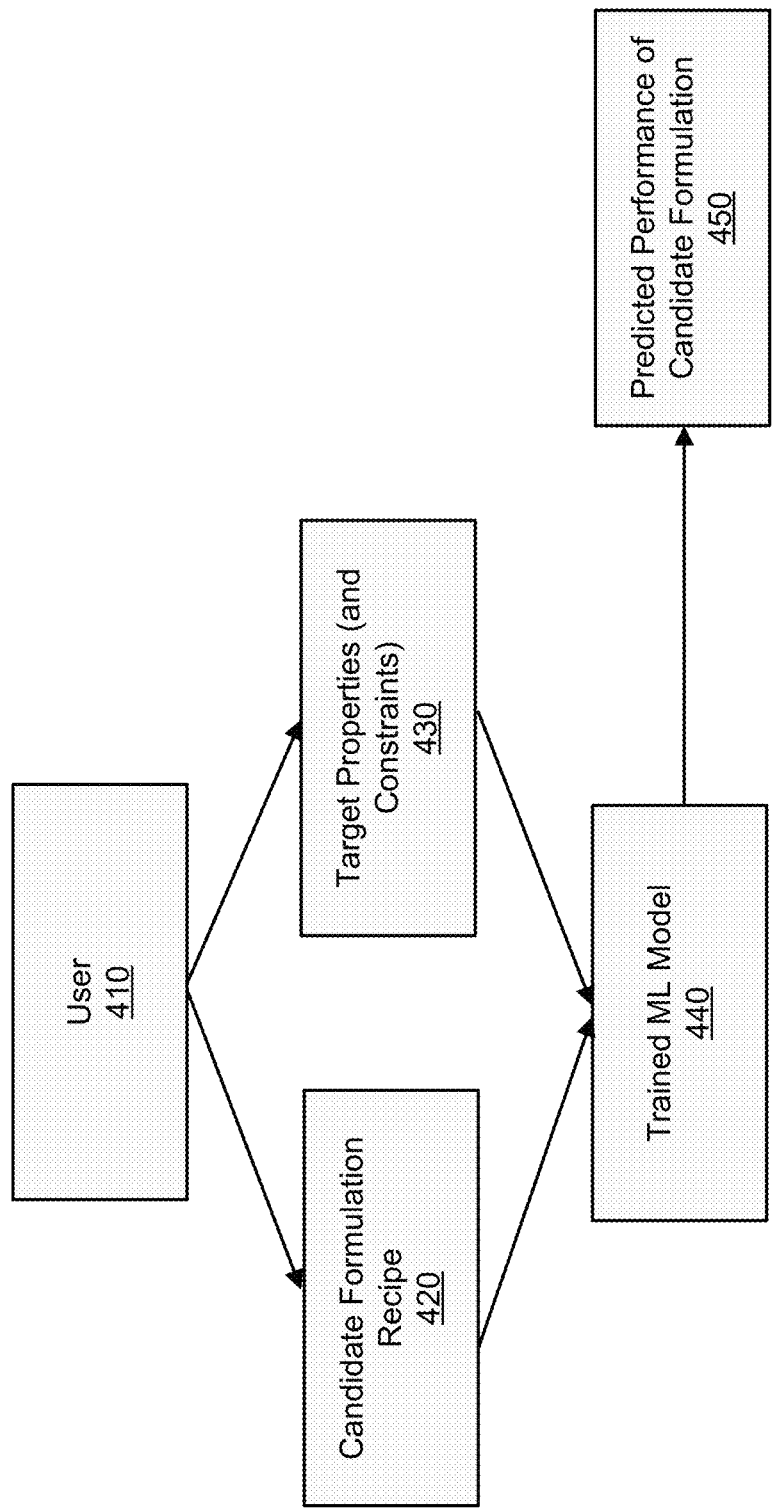
FIG. 4 is a data flow diagram illustrating an exemplary embodiment of using the trained machine learning model of the new recipe evaluation service.

Formulation prediction module 234 uses the trained machine learning model to predict resulting target properties from candidate formulation recipes (e.g., directly input, or derivable, based on input by a user). A given recipe may include the ingredient amounts and/or prescribed processing information. Turning briefly to FIG. 4, which illustrates an exemplary process for formulation prediction, FIG. 4 is a data flow diagram illustrating an exemplary embodiment of using the trained machine learning model of the new recipe evaluation service. In FIG. 4, a recipe using one or more new ingredients that have not been previously explored can be evaluated. The candidate recipe is input into the machine learning model, which performs featurization such that the machine learning model can predict the candidate formulation performance, even in the presence of new ingredients. A user 410 provides input of a candidate formulation recipe 420, candidate formulation recipe being a prescription of amounts of ingredients used, as well as any processing and/or mixing information. The user 410 also inputs target properties and/or constraints, 430. Inputs 420 and 430 are input into trained machine learning (ML) model 440. The machine learning model predicts the candidate formulation performance, evaluating whether it meets the target performance and constraints. Using mechanisms described above, the many possible combinations of ingredients are featurized into relatively few aggregated ingredient properties. These few aggregated ingredient properties are used to predict one or more formulation properties desired by the user (e.g., a particular color and/or strength of the formulation). Trained ML model 440 outputs a representation of predicted formulation performance in one or more target properties (e.g., where input 430 includes a specified tensile strength and optical clarity, corresponding representations of predicted performance may for these properties may be output, such as 98 megapascals+/−5 megapascals). For example, following the rubber example above, the target property could be a desired tear strength, and the constraints could be a minimum target tear strength and/or a maximum hardness. While not depicted, additional inputs may be received for input into the trained machine learning model, such as indicia, for each ingredient, of a property of the ingredient and its role in the formulation.

The predicted performance properties of the candidate formulation 450 may be expressed in terms of physical quantities or in terms of the likelihood of a specified target value being achieved if the formulation were actually created. In an embodiment, new recipe evaluation service 130 converts the output of the machine learning model into a likelihood that the specified target value will be achieved. For example, if the output of the machine learning model is that a candidate formulation will have a tensile strength of 98 megapascals+/−5 megapascals, and a target property of the candidate formulation is 100 megapascals, then new recipe evaluation service 130 may determine the likelihood based on this information (e.g., a likelihood of 32% that the target property will be achieved if the candidate formulation is made). The likelihood may be determined using any statistical formula or transformation of the representation output by the machine learning model. In an embodiment, the likelihood may be directly output by the machine learning model. The predicted performance may be based on, using the output of the trained machine learning model, featurization of the candidate new formulations relative to featurization of the ingredients.

Figure 5:
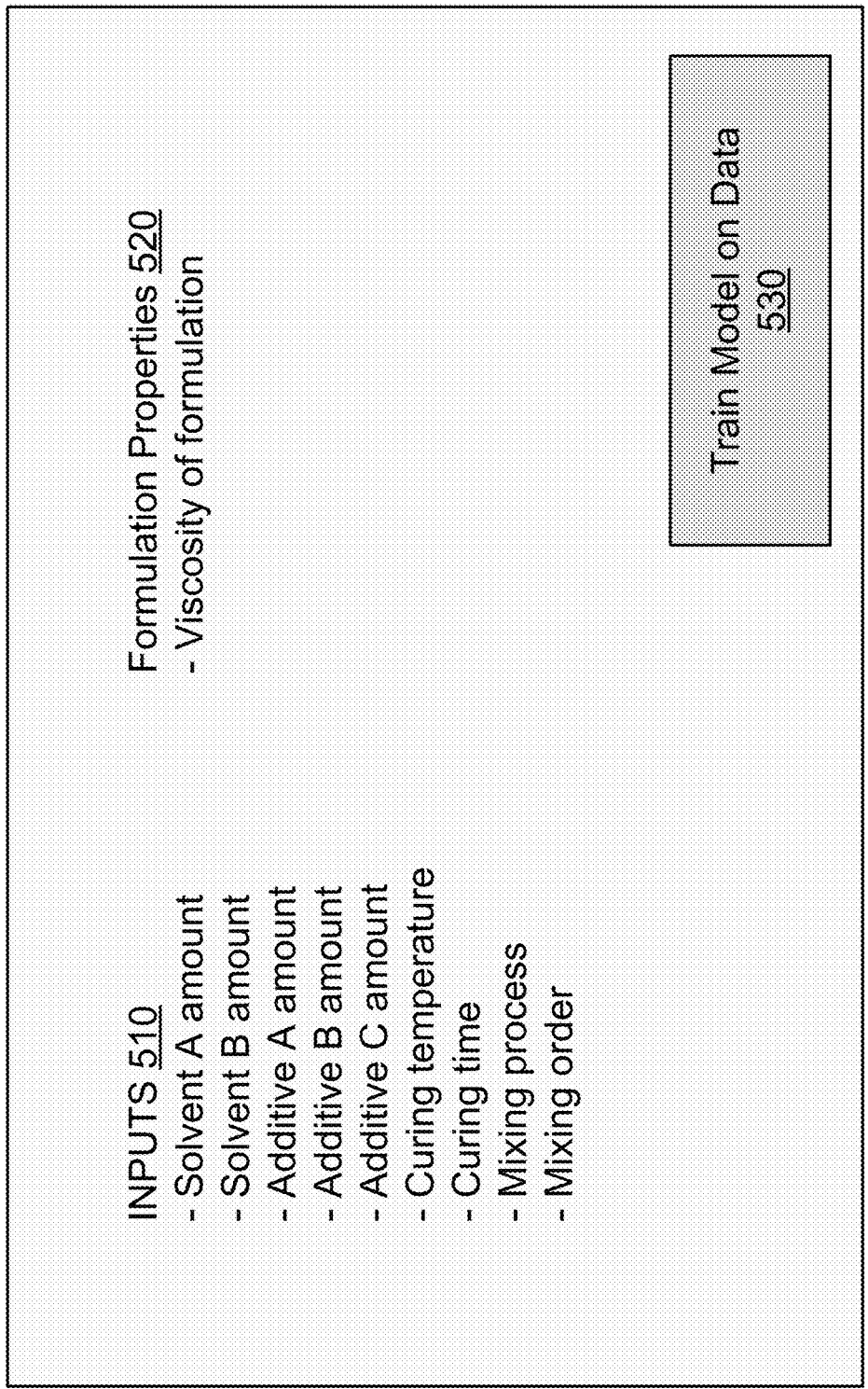
FIG. 5 illustrates an exemplary user interface including requested inputs and outputs of the new recipe evaluation service.

FIG. 5 illustrates an exemplary user interface including requested inputs and outputs of the new recipe evaluation service. User interface 500 depicts (e.g., based on execution of user interface module 231) an example where a user wishes to train a machine learning model (e.g., using training module 232) for a formulation having a particular viscosity, based on usage of one or more solvents and additives, the solvents having a specified average density, and the additives having a particular average particle size. The inputs may be entered manually by the user, or may be populated automatically by using a batch or partial-batch input of historical data 241. Input 520 corresponds to input 330 of FIG. 3, and formulation properties 530 corresponds to input 320 of FIG. 3. Selectable option 530, when selected, triggers the training of the machine learning model (e.g., using training module 232).

Predictions and/or likelihoods may be output in any meaningful way to the user. In an embodiment, formulation prediction module 234 generates a table (or other data structure) of recipes, where, for example each row is a single recipe and may also include its processing parameters. Reading across a given row will detail how much of each ingredient to mix, and how to process this mix, to yield a formulation. The table may also indicate predicted performances of each recipe relative to input target performance specifications. The table may be ranked based on likely performance of each formulation with respect to the target property. Formulation prediction module 234 may generate one or more scatter plots to show predicted performance of some or all candidate recipes in a single graphical space.

Example Use Cases

An illustrative, non-limiting, and non-exhaustive set of exemplary industry-relevant use cases follow that use the aforementioned modules and machine learning models to form predictions.

Rubber Formulations

A user needs to make a new rubber formulation to be used in vehicle tires. A key darkening agent, used to produce the final product's color, is no longer available. The user inputs historical data from previous formulations: various natural rubbers, curing agents, darkening agents, have been used to yield a variety of formulations with various mechanical properties including tear strength and impact strength. In more detail: The inputs to the model are the amounts of different ingredients used, along with the ingredients' physical and chemical properties and their roles in the formulations (e.g., a curative or colorant), as well as any relevant processing parameters. The outputs of the model are the predicted mechanical properties of the final formulation.

A formulations featurizer transforms these recipes from "% of each ingredient" to physically informed descriptors, including "% of total darkening agents" and "average particle size of darkening agents." The formulations-featurized input data is paired with the user-provided property data to create input-output pairs for training a ML model. The model is then trained.

The user now wishes to query the new recipe evaluation service 130 for new formulations, avoiding the usage of the darkening agent which is no longer available, and improving the impact strength while maintaining tear strength. The trained ML model considers many possible formulation recipes, provided by the user, and predicts each of their resulting tear strengths and impact strengths. The user receives a list of the formulations' performances and the likelihoods of meeting the target constraints. These formulations recipes, by virtue of the user's inputs, all avoid the use of the unavailable darkening agent. The user can now create new formulations, with a high/quantified level of confidence that they will meet product specification requirements, while also adapting to the disruption in their ingredient supply.

Coating Solutions

The workflow would be the same as in the rubber formulation scenario. In this scenario, a user may need to make a new solution that maintains the same viscosity, such that the coated material is evenly-coated. A key binding agent may no longer be usable due to new industry regulations. The user inputs would again be historical ingredient mixtures (reported as amounts of ingredients and property/role data for each ingredient) and processing parameters, along with formulation properties (e.g., physical properties such as viscosity). The goal may be to maintain viscosity, and the trained ML model would yield predicted formulation properties, which could be then used to rank a list of candidate recipes for manufacture, which all avoid the use of the binding agent that is no longer usable.

Compounded Polymer Blends

In this scenario, a user may need to mix a bulk resin with a small percentage of stabilizing additives to extend shelf-life of the product. The user inputs would be historical recipes (ingredient amounts mixed together) along with their recorded ingredient and formulation properties along with relevant processing parameters. One example would be a bulk resin that has 2% of additive A, and 3% of additive B, and both additives have known molecular structures (from which properties can be computed using known methods e.g., QSAR). The final mixed formulation may have a shelf-life of 25 days. A trained ML model could then be used to evaluate recipes that use new additives to further extend shelf-life.

Consumer Cosmetics

In this scenario, a user may be creating dry-powder makeup by mixing several dry powders together, including base pigments and particles to retain moisture. The user inputs would be historical recipes (ingredient amounts mixed together) along with their properties, and the optical properties (e.g., color, reflectance) of the resulting mix, and any relevant processing parameters. A trained ML model could then be used to evaluate new formulation recipes that target a specific color profile.

| EXEMPLARY SUMMARY OF MODEL INPUTS AND OUTPUTS FOR USE CASE EXAMPLES | | | |
| --- | --- | --- | --- |
| Application | User Inputs | Transformed features (Model Inputs) | Exemplary Outputs (e.g., as requested by the user) |
| Rubber formulations | Amounts of natural rubbers, colorants, and curing agents. Properties of each of the above ingredients (e.g., particle size of colorants) | Average particle size of colorants in a recipe Total amount of curing agents in a recipe Etc. | Mechanical properties, including impact strength and tear strength. |
| Coating solutions | Amounts of binders, solvents, and additives. Properties of each of the above ingredients (e.g., densities of solvents) | Average density of solvents in a recipe Total amount of binders in a recipe Total amount of additives in a recipe Etc. | Physical properties, including optical, thermal, electrical, and mechanical properties: including viscosity, boiling points, transparency, electrical conductivity, thermal conductivity. |
| Compounded polymer blends | Amounts of resin and additives. Properties of each of the additives (e.g., derived from their molecular formulas). | Average molecular weight of additive molecules Total amount of resins used in recipe Etc. | Shelf-life time estimates. |
| Consumer cosmetics | Amounts of pigments and moisture-retaining particles. Properties of each ingredient (e.g., particle size, raw pigment color). | Average particle size of pigments Average redness of pigments Average blueness of pigments Etc. | Overall color and reflectance. |

Computing Machine Architecture

Figure 6:
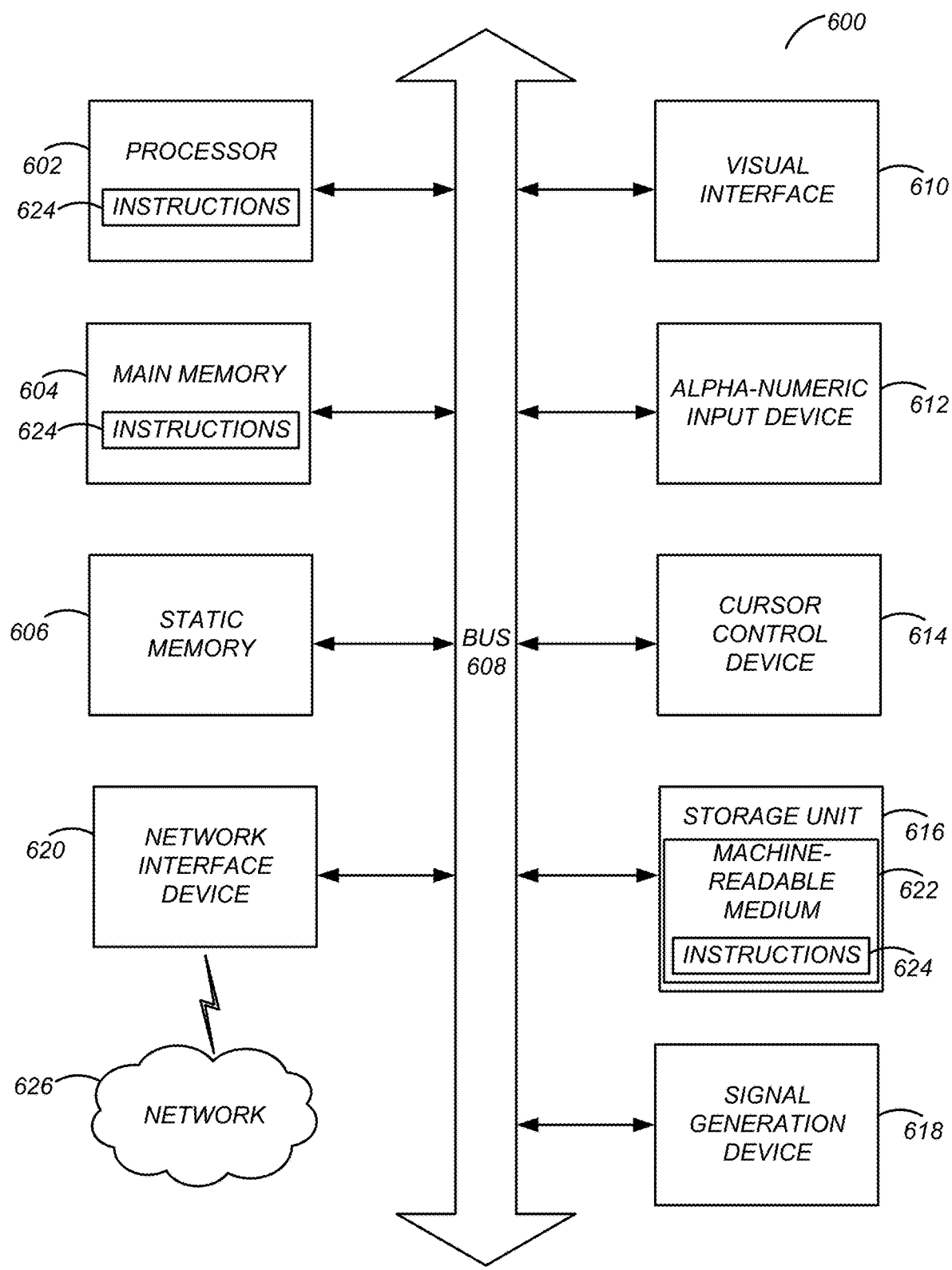
FIG. 6 is a block diagram illustrating components of an example machine able to read instructions from a machine-readable medium and execute them in a processor (or controller).

FIG. 6 is a block diagram illustrating components of an example machine able to read instructions from a machine-readable medium and execute them in a processor (or controller). Specifically, FIG. 6 shows a diagrammatic representation of a machine in the example form of a computer system 600 within which program code (e.g., software) for causing the machine to perform any one or more of the methodologies discussed herein may be executed. The program code may be comprised of instructions 624 executable by one or more processors 602. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 624 (sequential or otherwise) that specify actions to be taken by that machine. Further, while only a single machine is illustrated, the term "machine" shall also be taken to include any collection of machines that individually or jointly execute instructions 624 to perform any one or more of the methodologies discussed herein.

The example computer system 600 includes a processor 602 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 604, and a static memory 606, which are configured to communicate with each other via a bus 608. The computer system 600 may further include visual display interface 610. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 610 may include or may interface with a touch enabled screen. The computer system 600 may also include alphanumeric input device 612 (e.g., a keyboard or touch screen keyboard), a cursor control device 614 (e.g., a mouse, a trackball, a joystick, a motion sensor, or other pointing instrument), a storage unit 616, a signal generation device 618 (e.g., a speaker), and a network interface device 620, which also are configured to communicate via the bus 608.

The storage unit 616 includes a machine-readable medium 622 on which is stored instructions 624 (e.g., software) embodying any one or more of the methodologies or functions described herein. The instructions 624 (e.g., software) may also reside, completely or at least partially, within the main memory 604 or within the processor 602 (e.g., within a processor's cache memory) during execution thereof by the computer system 600, the main memory 604 and the processor 602 also constituting machine-readable media. The instructions 624 (e.g., software) may be transmitted or received over a network 626 via the network interface device 620.

While machine-readable medium 622 is shown in an example embodiment to be a single medium, the term "machine-readable medium" should be taken to include a single medium or multiple media (e.g., a centralized or distributed database, or associated caches and servers) able to store instructions (e.g., instructions 624). The term "machine-readable medium" shall also be taken to include any medium that is capable of storing instructions (e.g., instructions 624) for execution by the machine and that cause the machine to perform any one or more of the methodologies disclosed herein. The term "machine-readable medium" includes, but not be limited to, data repositories in the form of solid-state memories, optical media, and magnetic media.

Exemplary Data Flow

Figure 7:
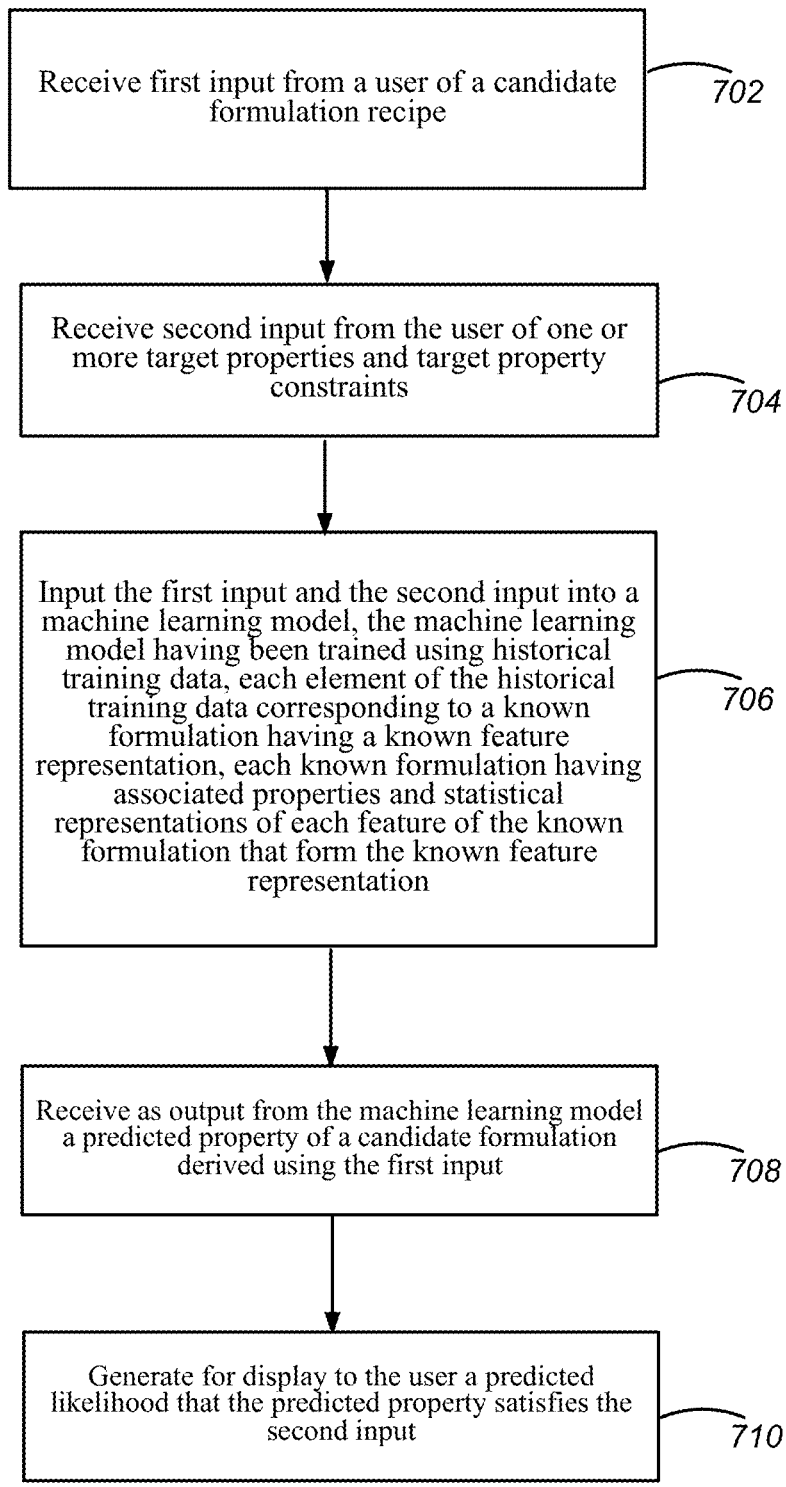
FIG. 7 is an exemplary data flow diagram showing an exemplary process for using the new recipe evaluation service.

FIG. 7 is an exemplary data flow diagram showing an exemplary process for using the new recipe evaluation service. Process 700 begins with new recipe evaluation service 130 receiving 702 (e.g., using user interface module 231) first input from a user of a candidate formulation recipe, and receiving 804 a second input from the user of one or more target properties and constraints on those target properties. In an embodiment, the constraints may include range, minimum, or maximum desired values for the target properties. In an embodiment, the target property constraints may comprise a performance requirement for the formulation or a minimization or maximization target for the performance property. The target property may be a physical or chemical property. Additional inputs may be received, such as inputs that specify, for each ingredient, a property of the ingredient, a role of the ingredient, and so on. The candidate formulation recipe may comprise one or more ingredients that were previously untested or new to the user, or for which the user had insufficient data.

New recipe evaluation service 130 inputs 706 the first input and the second input into a machine learning model, the machine learning model having been trained (e.g., using training module 232) using historical training data (e.g., historical data 241), each element of the historical training data corresponding to a known formulation having a known feature representation, each known formulation having associated properties and statistical representations of each feature of the known formulation that form the known feature representation. The associated properties and statistical representations may be determined by transforming the property and the role of each ingredient, for example, into a component feature representation, where each component feature representation, when taken in the aggregate, forms the known feature representation.

New recipe evaluation service 130 receives 708 as output from the machine learning model a prediction of the target properties. New recipe evaluation service 130 may generate for display to the user a predicted likelihood that the predicted property satisfies the second input. The predicted likelihood may have been directly output from the machine learning model, or may be derived by new recipe evaluation service 130 from the prediction of the target properties.

ADDITIONAL CONFIGURATION CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for predicting performance of various candidate recipes using untested ingredients through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
receiving first input from a user of a candidate formulation recipe;
receiving second input from the user of one or more target properties and target property constraints;
inputting the first input and the second input into a machine learning model, the machine learning model having been trained using historical training data, each element of the historical training data corresponding to a known formulation having a known feature representation, each known formulation having associated properties and statistical representations of each feature of the known formulation that form the known feature representation;
receiving as output from the machine learning model a predicted property of a candidate formulation; and
generating for display to the user a predicted likelihood that the predicted property satisfies the second input.

2. The method of claim 1, wherein the target property constraints comprise at least one of: ranges of acceptable values, maximum acceptable values of the one or more target properties, minimum acceptable values of the one or more target properties, a minimization goal, and a maximization goal.

3. The method of claim 1, wherein the target property constraints comprise a performance requirement for the candidate formulation.

4. The method of claim 1, wherein the candidate formulation recipe comprises one or more ingredients that were previously untested or new to the user.

5. The method of claim 4, wherein the historical training data comprises third input received from the user that specifies, for each ingredient, one or more properties of the ingredient, and a role of the ingredient.

6. The method of claim 5, wherein the associated properties and the statistical representations of each feature are determined by transforming the property and the role of each ingredient into a component feature representation, and wherein each component feature representation, when taken in the aggregate, forms the known feature representation.

7. The method of claim 6, wherein the target property is at least one of a physical or chemical property.

8. The method of claim 7, wherein a materials class of interest is rubbers, and wherein the target properties comprise mechanical properties specific to the materials class of rubbers comprising at least one of impact strength and tear strength.

9. The method of claim 1, wherein a plurality of candidate formulations performance predictions are derived using the first input, wherein a respective likelihood that the predicted property satisfies the constraint is determined for each respective one of the multiple candidate formulations using the second input, and wherein the method further comprises:
ranking the plurality of candidate formulations based on their respective likelihoods; and
generating for display to the user a list of the plurality of candidate formulations using the ranking.

10. A non-transitory computer-readable medium comprising memory with instructions encoded thereon, the instructions, when executed by one or more processors, causing operations the one or more processors to perform operations, the instructions comprising instructions to:
receive first input from a user of a candidate formulation recipe;
receive second input from the user of one or more target properties and target property constraints;
input the first input and the second input into a machine learning model, the machine learning model having been trained using historical training data, each element of the historical training data corresponding to a known formulation having a known feature representation, each known formulation having associated properties and statistical representations of each feature of the known formulation that form the known feature representation;
receive as output from the machine learning model a predicted property of a candidate formulation, and a likelihood that the predicted property satisfies a constraint using the second input; and
output for display to the user a predicted likelihood that the predicted property satisfies the second input.

11. The non-transitory computer-readable medium of claim 10, wherein the target property constraints comprise at least one of: ranges of acceptable values, maximum acceptable values of the one or more target properties, minimum acceptable values of the one or more target properties, a minimization goal, and a maximization goal.

12. The non-transitory computer-readable medium of claim 10, wherein the target property constraints comprise a performance requirement for the candidate formulation.

13. The non-transitory computer-readable medium of claim 10, wherein the candidate formulation recipe comprises one or more ingredients that were previously untested or new to the user.

14. The non-transitory computer-readable medium of claim 13, wherein the historical training data comprises third input received from the user that specifies, for each ingredient, one or more properties of the ingredient, and a role of the ingredient.

15. The non-transitory computer-readable medium of claim 14, wherein the associated properties and the statistical representations of each feature are determined by transforming the property and the role of each ingredient into a component feature representation, and wherein each component feature representation, when taken in the aggregate, forms the known feature representation.

16. The non-transitory computer-readable medium of claim 15, wherein the target property is at least one of a physical or chemical property.

17. The non-transitory computer-readable medium of claim 16, wherein a materials class of interest is rubbers, and wherein the target properties comprise mechanical properties specific to the materials class of rubbers comprising at least one of impact strength and tear strength.

18. The non-transitory computer-readable medium of claim 10, wherein a plurality of candidate formulation property predictions are derived using the first input, wherein a respective likelihood that the predicted property satisfies the constraint is determined for each respective one of the multiple candidate formulations, and wherein the instructions further comprise instructions to:
rank the plurality of candidate formulations based on their respective likelihoods; and
generate for display to the user a list of the plurality of candidate formulations using the ranking.

19. A system comprising:
memory with instructions encoded thereon; and
one or more processors that, when executing the instructions, are caused to perform operations comprising:
receiving first input from a user of a candidate formulation recipe;
receiving second input from the user of one or more target properties and target property constraints;
inputting the first input and the second input into a machine learning model, the machine learning model having been trained using historical training data, each element of the historical training data corresponding to a known formulation having a known feature representation, each known formulation having associated properties and statistical representations of each feature of the known formulation that form the known feature representation;
receiving as output from the machine learning model a predicted property of a candidate formulation, and a likelihood that the predicted property satisfies a constraint using the second input; and
outputting for display to the user a predicted likelihood that the predicted property satisfies the second input.

20. The system of claim 19, wherein the candidate formulation recipe comprises one or more ingredients that were previously untested or new to the user.

* * * * *